US011364271B2

(12) United States Patent
Le Berre et al.

(10) Patent No.: US 11,364,271 B2
(45) Date of Patent: Jun. 21, 2022

(54) **METHODS OF TREATING *PSEUDOMONAS AERUGINOSA* RESPIRATORY INFECTIONS**

(71) Applicants: INSERM (Institut National de la Santé et de la Recherche Médicale), Paris (FR); Etablissement Français du Sang (EFS), La Plaine Saint Denis (FR); Université de Bretagne Occidentale, Brest (FR); Centre Hospitalier Regional et Universitaire de Brest, Brest (FR)

(72) Inventors: Rozenn Le Berre, Brest (FR); Marie-Sarah Fangous, Quimper (FR); Gwenaelle Le Blay, Plouzané (FR); Geneviève Hery-Arnaud, Brest (FR); Rosyne Lagrafeuille, Brest (FR)

(73) Assignees: INSERM, Paris (FR); Etablissement Français Du Sang (EFS), La Plaine Saint Denis (FR); Université De Bretagne Occidentale, Brest (FR); Centre Hospitalier Regional et Universitaire de Brest, Brest (FR)

( * ) Notice: Subject to any disclaimer, the term of this patent is extended or adjusted under 35 U.S.C. 154(b) by 0 days.

(21) Appl. No.: 17/049,221

(22) PCT Filed: Apr. 19, 2019

(86) PCT No.: PCT/EP2019/060214
§ 371 (c)(1),
(2) Date: Oct. 20, 2020

(87) PCT Pub. No.: WO2019/202137
PCT Pub. Date: Oct. 24, 2019

(65) Prior Publication Data
US 2021/0236567 A1 Aug. 5, 2021

(30) Foreign Application Priority Data
Apr. 20, 2018 (EP) .................................... 18305486

(51) Int. Cl.
*A01N 63/00* (2020.01)
*A61K 35/747* (2015.01)
*A61P 31/04* (2006.01)
*A61P 11/00* (2006.01)

(52) U.S. Cl.
CPC ............ *A61K 35/747* (2013.01); *A61P 11/00* (2018.01); *A61P 31/04* (2018.01)

(58) Field of Classification Search
CPC ..................................................... A61K 35/747
See application file for complete search history.

(56) References Cited

FOREIGN PATENT DOCUMENTS

| WO | 2004/087178 A1 | 10/2004 |
| WO | 2016/077190 A1 | 5/2016 |
| WO | 2017/134466 A1 | 8/2017 |

OTHER PUBLICATIONS

Database WPI, Week 201366, Thomson Scientific, May 8, 2013.
Alvarez et al.; "Effect of Lactobacillus casei and yogurt administration on prevention of Pseudomonas aeruginosa infection in young mice"; Journal of Food Protection, vol. 64, No. 11, Nov. 1, 2011, pp. 1768-1774.
Youenn et al.; "Screening of *Lactobacillus* spp. for the prevention of Pseudomonas aeruginosa pulmonary infections"; BMC Microbiology, vol. 14, No. 1, Apr. 27, 2014, p. 107.
Khailova et al.; "Lactobacillus rhamnosus GG treatment improves intestinal permeability and modulates inflammatory response and homeostasis of spleen and colon in experimental model of Pseudomonas aerugionsa pneumonia"; Clinical Nutrition, vol. 36, No. 6, 2017, pp. 1549-1557.

*Primary Examiner* — Albert M Navarro
(74) *Attorney, Agent, or Firm* — WC&F IP

(57) ABSTRACT

*Pseudomonas aeruginosa* (PA) leads to chronic respiratory infections especially in patients with cystic fibrosis patients and chronic obstructive pulmonary disease (COPD), characterized by a high morbidity. After screening Lactobacilli coming from CF expectoration, on their capacity to inhibit two *Pseudomonas aeruginosa* (PA) virulence factors (elastase, pyocyanin), the inventors evaluated the effect of intranasal administration of Lactobacilli on PA murine pneumonia. The primary outcome was the bacterial lung load 24 hours after PA induced pneumonia. To understand the role of *Lactobacillus*, the chemokines, the pro and anti-inflammatory BAL rates were also measured. The administration of Lactobacilli cocktail 18 h prior the PA lung infection decreases significantly the lung bacterial load at 24 h post-infection. Although the mechanisms need to be deeply explored, an immunomodulation effect may be involved, notably through the recruitment of neutrophils. Thus the present relates to a method of treating a *Pseudomonas aeruginosa* respiratory tract infection in a patient in need thereof comprising administering to the patient's respiratory tract a therapeutically effective amount of at least one *Lactobacillus* strain.

7 Claims, 4 Drawing Sheets

METHODS OF TREATING *PSEUDOMONAS AERUGINOSA* RESPIRATORY INFECTIONS

FIELD OF THE INVENTION

Figure 1:
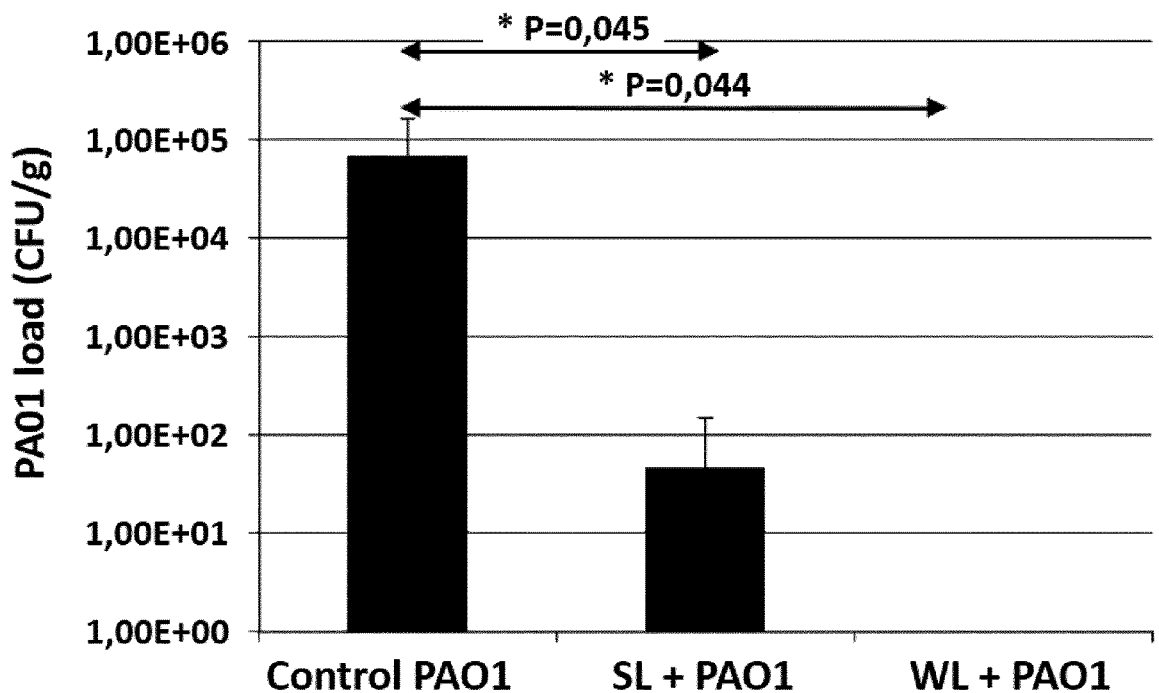
Figure 2A:
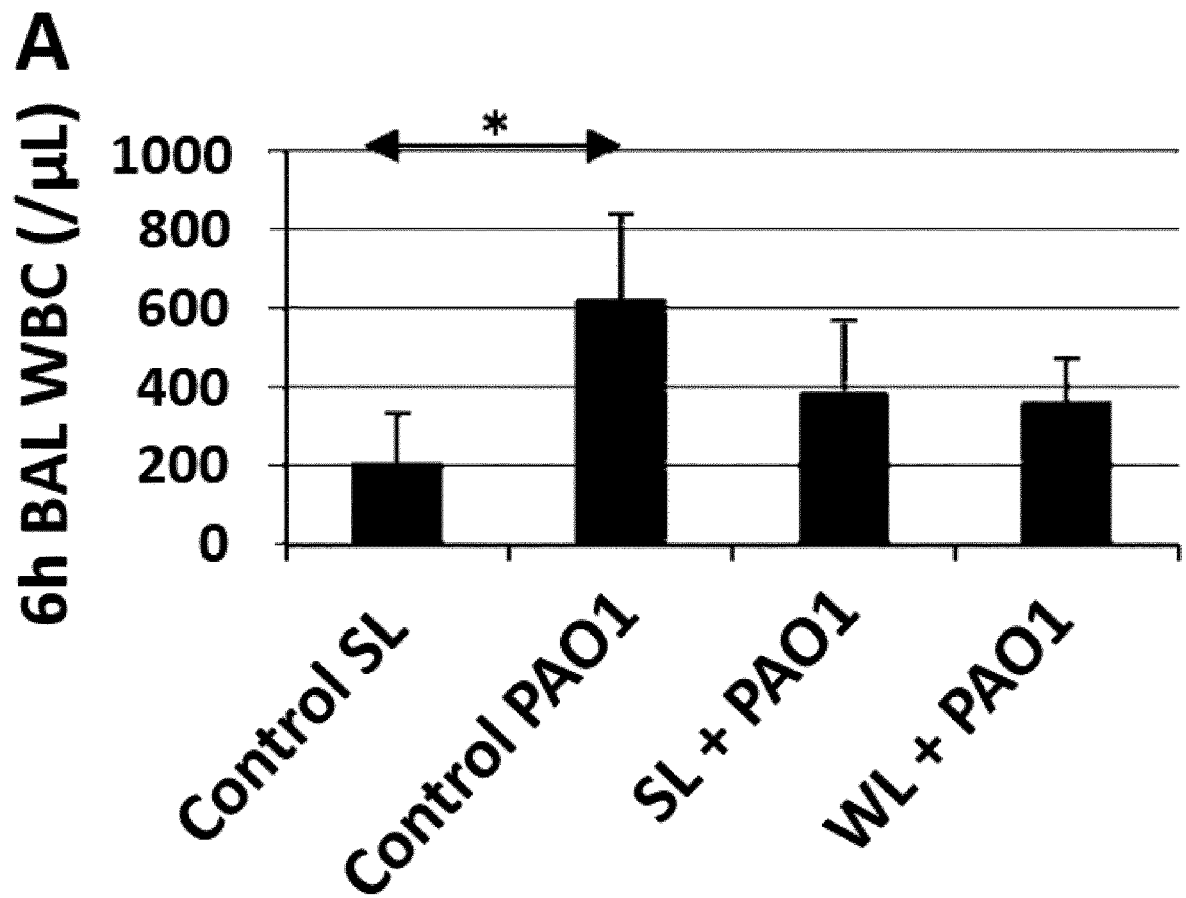
Figure 2B:
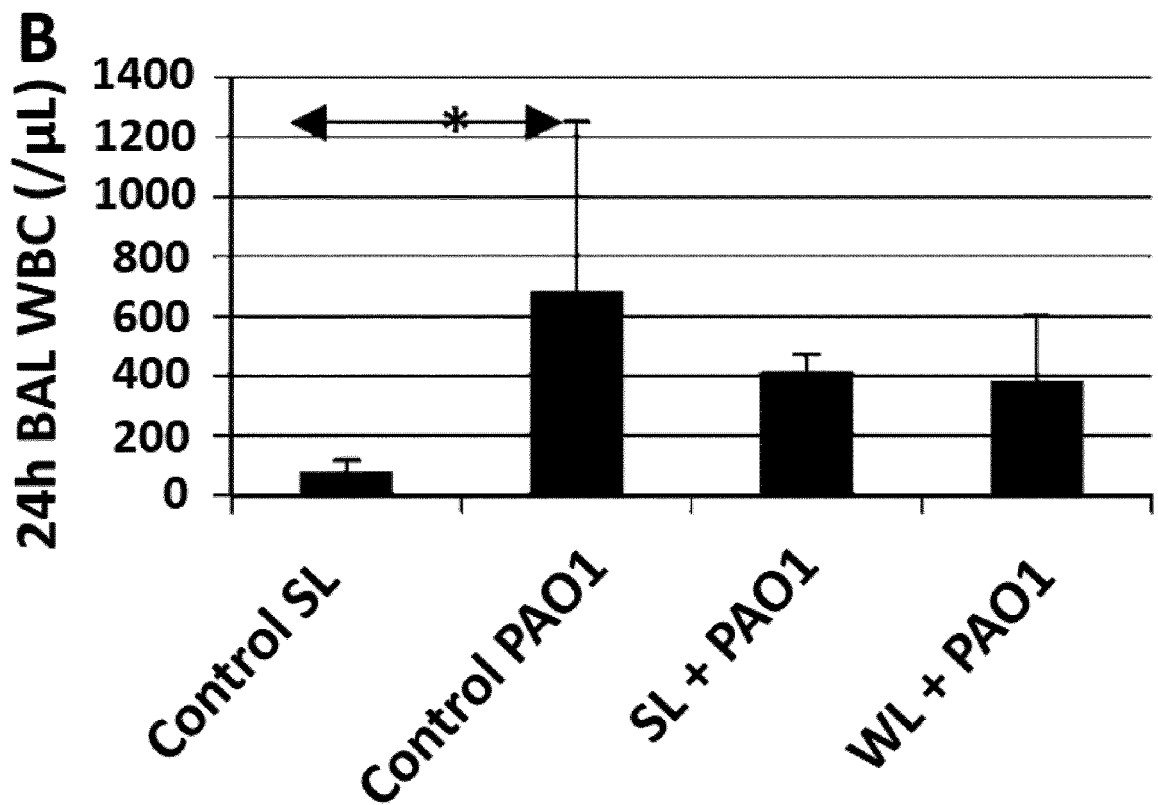
Figure 2C:
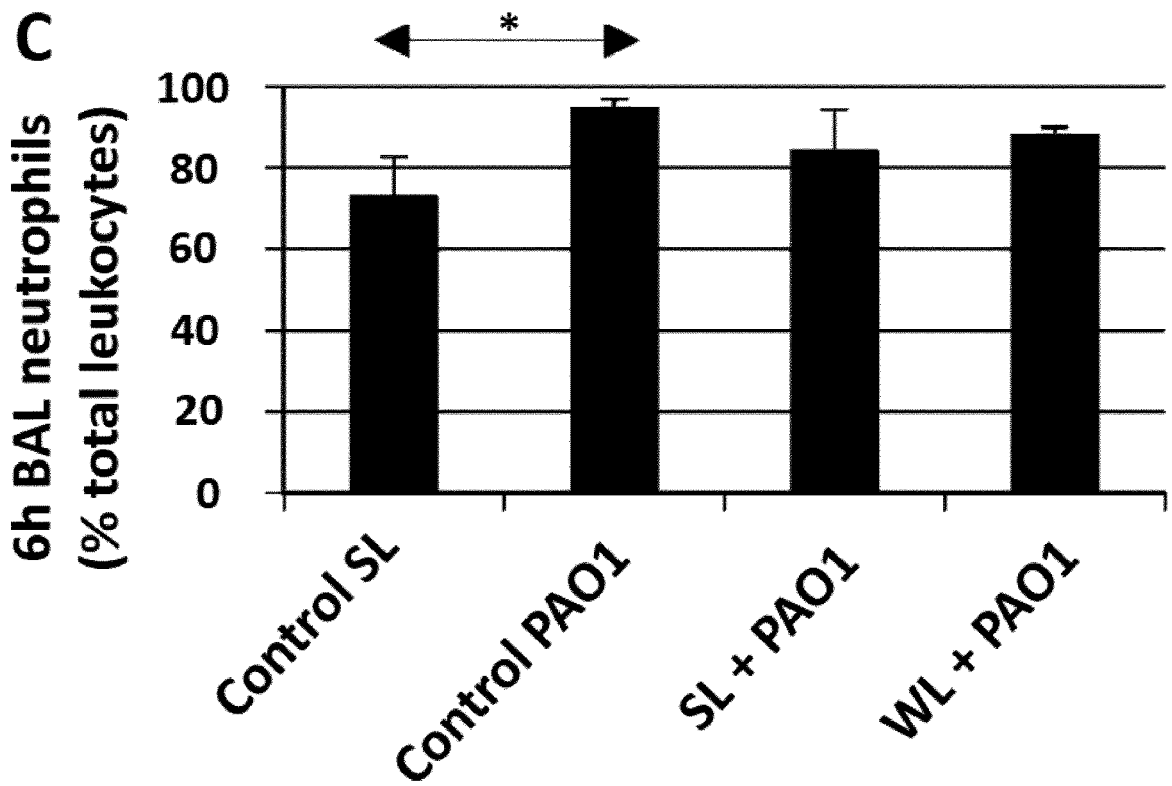
Figure 2D:
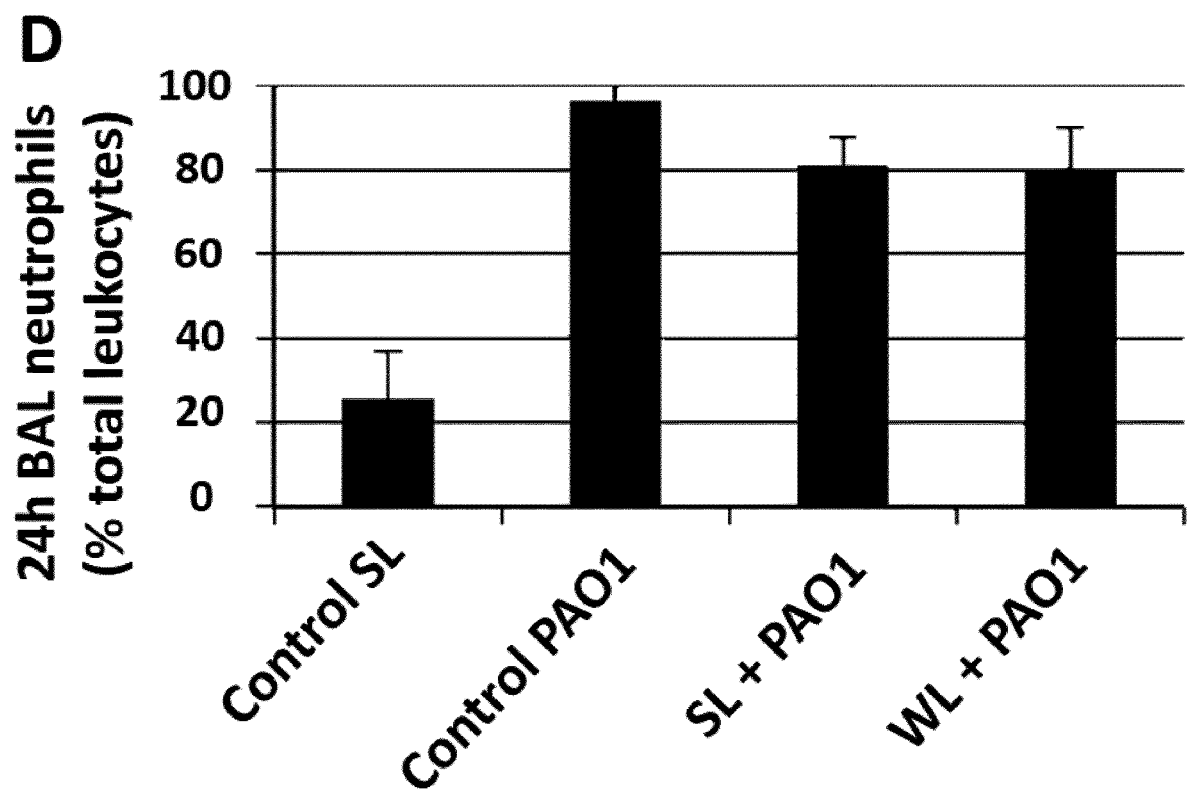

The present invention relates to methods of treating *Pseudomonas aeruginosa* respiratory tract infections.

BACKGROUND OF THE INVENTION

*Pseudomonas aeruginosa* (PA) leads to chronic respiratory infections especially in patients with cystic fibrosis patients and chronic obstructive pulmonary disease (COPD), characterized by a high morbidity (Langan K M, *Current opin Infect Dise* 2015, Saiman, *Clin Microbiol Rev* 2004); this bacteria is also the main pathogen of ventilated acquired pneumonia (VAP), associated with a high mortality (Fujitani, *Chest* 2011). Rates of antibiotic resistance in PA are increasing (EARSS data . . . ) leading to therapeutic deadlock.

Among the antibiotherapy alternative solutions are the probiotics, defined as live microbial food components which are beneficial for human health (Erickson, *J Nutr* 2000; Alexandre, *MMI* 2013). Lactobacilli, the most studied probiotic are non-pathogenic Gram-positive bacteria, their natural reservoir are food (milk, cheese . . . ) and human (intestine, vagina . . . ). They can exert their beneficial effect on the host through different ways especially their immunomodulatory or their antibacterial activity (Liévin-Le Moal, Servin, *Clin Microbiol* Rev). Valdez et al (*CMI*, 2005) showed that *L. plantarum* inhibited two PA virulence factors controlled by quorum sensing (elastase and biofilm). Among Lactobacilli from oral human cavities and from raws milk, 8 strains were screened harbouring anti-elastase and anti-biofilm properties (Alexandre, *BMC Microbiol* 2014). Khailova et al (Shok, 2013), showed that oral administration of *L. rhamnosus* GG improved outcome 7-day survival following PA-induced pneumonia; regulatory T cells may play a role in that protection. Randomized trials suggest that probiotics (one or several *Lactobacillus* species most of the time) decrease the incidence of VAP (Bo, *Cochrane revue*, 2014) but many bias are reported: single centre study, route of administration and duration of intake are different . . . (Bo, *Cochrane*, 2014; Cook, *Trials* 2016). If the oral route is often studied to analyse the Lactobacilli effect, the nasal route could provide benefits for the respiratory infection by stimulating Nasopharynx Associated Lymphoid Tissue (NALT) instead of GALT (Kiyono, *Nat Rev Immunol* 2004). The intranasal administration of *Lactobacillus* species before intranasal inoculation of Influenza Virus or Pneumonia virus of mice decreased the mortality on these two pneumonia murine models (Izumo, *Internat Immunopharmacol* 2010; Dyer, *J of Virol* 2016 . . . ).

SUMMARY OF THE INVENTION

The present invention relates to methods of treating *Pseudomonas aeruginosa* respiratory tract infections. In particular, the present invention is defined by the claims.

DETAILED DESCRIPTION OF THE INVENTION

After screening Lactobacilli coming from CF expectorations, on their capacity to inhibit two *Pseudomonas aeruginosa* (PA) virulence factors (elastase, pyocyanin), the inventors evaluated the effect of intranasal administration of Lactobacilli on PA murine pneumonia. The primary outcome was the bacterial lung load 24 hours after PA induced pneumonia. To understand the role of *Lactobacillus*, the chemokines, the pro and anti-inflammatory BAL rates were also measured. The administration of Lactobacilli cocktail 18 h prior the PA lung infection decreases significantly the lung bacterial load at 24 h post-infection. Although the mechanisms need to be deeply explored, an immunomodulation effect may be involved, notably through the recruitment of neutrophils.

Accordingly, a first object of the present invention relates to a method of treating a *Pseudomonas aeruginosa* respiratory tract infection in a patient in need thereof comprising administering to the patient's respiratory tract a therapeutically effective amount of at least one *Lactobacillus* strain.

As used herein, the term "*Pseudomonas aeruginosa*" or "PA" has its general meaning in the art and refers to a common Gram-negative, rod-shaped bacterium.

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., pain, disease manifestation, etc.]).

In some embodiments, the subject suffers from a chronic pulmonary disease selected from the group consisting of chronic obstructive pulmonary disease (COPD), ventilated acquired pneumonia, chronic bronchitis, recurrent bronchitis, acute bronchitis, rhinosinusitis, mild pulmonary disease, hereditary emphysema, and cystic fibrosis. In some embodiments, the patient suffers from or is at risk of suffering from cystic fibrosis. In some embodiments, the subject suffers or is at risk of suffering from a disease associated with reduced CFTR function due to mutations in the gene encoding CFTR or environmental factors (e.g., smoke). A mutation thereof capable of regulator activity, including, but not limited to, F508del-CFTR, R117H CFTR, and G551D CFTR (see, e.g., http://www.genet.sickkids.on.ca/cftr, for CFTR mutations). These diseases include, cystic fibrosis, chronic bronchitis, recurrent bronchitis, acute bronchitis, chronic rhinosinusitis, allergic bronchopulmonary aspergillosis, bronchopulmonary aspergillosis (ABPA) and asthma. In some embodiments, the subject harbors at least one mutation in the CFTR gene, including, but not limited to F508del-CFTR, R117H CFTR, and G551D CFTR As used herein, the term "*Lactobacillus*" refers to members of the genus *Lactobacillus*, in the family Lactobacillaceae. These bacteria are Gram-positive optionally anaerobic bacteria that represent a major part of the bacterial group often referred to as "lactic acid bacteria". The genus includes any of the following species: *Lactobacillus acetotolerans, Lactobacillus acidifarinae, Lactobacillus acidipiscis, Lactobacillus acidophilus, Lactobacillus agilis, Lactobacillus algidus, Lactobacillus alimentarius, Lactobacillus allii, Lactobacillus amylolyticus, Lactobacillus amylophilus, Lactobacillus amylotrophicus, Lactobacillus amylovorus, Lactobacillus animalis, Lactobacillus antri, Lactobacillus apinorum, Lactobacillus apis, Lactobacillus apodemi, Lactobacillus aquaticus, Lactobacillus arizonensis, Lactobacillus aviarius, Lactobacillus aviarius* subsp. *araffinosus, Lactobacillus aviarius* subsp. *aviaries, Lactobacillus backii, Lactobacillus bambusae, Lactobacillus bavaricus, Lactobacillus bifermentans, Lactobacillus bobalius, Lactobacillus bombi, Lactobacillus bombicola, Lactobacillus brantae, Lactobacillus brevis, Lactobacillus buchneri, Lactobacillus bulgaricus, Lactobacillus cacaonum, Lactobacillus camelliae, Lactobacillus capillatus, Lactobacillus carnis, Lactobacillus casei, Lactobacillus casei* subsp. *alactosus, Lactobacillus casei* subsp. *casei, Lactobacillus casei* subsp. *pseudoplantarum, Lactobacillus casei* subsp. *rhamnosus, Lactobacillus casei* subsp. *tolerans, Lactobacillus catenaformis, Lactobacillus caviae, Lactobacillus cellobiosus, Lactobacillus cerevisiae, Lactobacillus ceti, Lactobacillus coelohominis, Lactobacillus colini, Lactobacillus collinoides, Lactobacillus composti, Lactobacillus concavus, Lactobacillus confuses, Lactobacillus coryniformis, Lactobacillus coryniformis* subsp. *coryniformis, Lactobacillus coryniformis* subsp. *torquens, Lactobacillus crispatus, Lactobacillus crustorum, Lactobacillus curieae, Lactobacillus curtus, Lactobacillus curvatus, Lactobacillus curvatus* subsp. *curvatus, Lactobacillus curvatus* subsp. *melibiosus, Lactobacillus cypricasei, Lactobacillus delbrueckii, Lactobacillus delbrueckii* subsp. *bulgaricus, Lactobacillus delbrueckii* subsp *delbrueckii, Lactobacillus delbrueckii* subsp. *indicus, Lactobacillus delbrueckii* subsp. *jakobsenii, Lactobacillus delbrueckii* subsp. *lactis, Lactobacillus delbrueckii* subsp. *sunkii, Lactobacillus dextrinicus, Lactobacillus diolivorans, Lactobacillus divergens, Lactobacillus durianus, Lactobacillus equi, Lactobacillus equicursoris, Lactobacillus equigenerosi, Lactobacillus fabifermentans, Lactobacillus faecis, Lactobacillus farciminis, Lactobacillus farraginis, Lactobacillus ferintoshensis, Lactobacillus fermentum, Lactobacillus floricola, Lactobacillus florum, Lactobacillus formosensis, Lactobacillus formicalis, Lactobacillus fructivorans, Lactobacillus fructosus, Lactobacillus frumenti, Lactobacillus fuchuensis, Lactobacillus furfuricola, Lactobacillus futsaii, Lactobacillus gallinarum, Lactobacillus gasseri, Lactobacillus gastricus, Lactobacillus ghanensis, Lactobacillus gigeriorum, Lactobacillus gorillae, Lactobacillus graminis, Lactobacillus halotolerans, Lactobacillus hammesii, Lactobacillus hamsteri, Lactobacillus harbinensis, Lactobacillus hayakitensis, Lactobacillus heilongjiangensis, Lactobacillus helsingborgensis, Lactobacillus helveticus, Lactobacillus helveticus* subsp. *jugurti, Lactobacillus herbarum, Lactobacillus heterohiochii, Lactobacillus hilgardii, Lactobacillus hokkaidonensis, Lactobacillus hominis, Lactobacillus homohiochii, Lactobacillus hordei, Lactobacillus iners, Lactobacillus ingluviei, Lactobacillus insicii, Lactobacillus intestinalis, Lactobacillus iwatensis, Lactobacillus ixorae, Lactobacillus japonicus, Lactobacillus jensenii, Lactobacillus johnsonii, Lactobacillus kalixensis, Lactobacillus kandleri, Lactobacillus kefiranofaciens, Lactobacillus kefiranofaciens* subsp. *kefiranofaciens, Lactobacillus kefiranofaciens* subsp. *kefirgranum, Lactobacillus kefirgranum, Lactobacillus kefiri, Lactobacillus kimbladii, Lactobacillus kimchicus, Lactobacillus kimchiensis, Lactobacillus kimchii, Lactobacillus kisonensis, Lactobacillus kitasatonis, Lactobacillus koreensis, Lactobacillus kullabergensis, Lactobacillus kunkeei, Lactobacillus lactis, Lactobacillus leichmannii, Lactobacillus letivazi, Lactobacillus lindneri, Lactobacillus malefermentans, Lactobacillus mali, Lactobacillus maltaromicus, Lactobacillus manihotivorans, Lactobacillus mellifer, Lactobacillus mellis, Lactobacillus melliventris, Lactobacillus metriopterae, Lactobacillus micheneri, Lactobacillus mindensis, Lactobacillus minor, Lactobacillus minutus, Lactobacillus mixtipabuli, Lactobacillus modestisalitolerans, Lactobacillus mucosae, Lactobacillus murinus, Lactobacillus musae, Lactobacillus nagelii, Lactobacillus namurensis, Lactobacillus nantensis, Lactobacillus nasuensis, Lactobacillus nenjiangensis, Lactobacillus nodensis, Lactobacillus odoratitofui, Lactobacillus oeni, Lactobacillus oligofermentans, Lactobacillus oris, Lactobacillus oryzae, Lactobacillus otakiensis, Lactobacillus ozensis, Lactobacillus panis, Lactobacillus panisapium, Lactobacillus pantheri, Lactobacillus parabrevis, Lactobacillus parabuchneri, Lactobacillus paracasei, Lactobacillus paracasei* subsp. *paracasei, Lactobacillus paracasei* subsp. *pseudoplantarum, Lactobacillus paracasei* subsp. *tolerans, Lactobacillus paracollinoides, Lactobacillus parafarraginis, Lactobacillus parakefiri, Lactobacillus paralimentarius, Lactobacillus paraplantarum, Lactobacillus pasteurii, Lactobacillus paucivorans, Lactobacillus pentosiphilus, Lactobacillus pentosus, Lactobacillus perolens, Lactobacillus piscicola, Lactobacillus plajomi, Lactobacillus plantarum, Lactobacillus plantarum* subsp. *argentoratensis, Lactobacillus plantarum* subsp. *plantarum, Lactobacillus plantarum* subsp. *plantarum, Lactobacillus pontis, Lactobacillus porcinae, Lactobacillus psittaci, Lactobacillus quenuiae, Lactobacillus rapi, Lactobacillus rennini, Lactobacillus reuteri, Lactobacillus rhamnosus, Lactobacillus rimae, Lactobacillus rodentium, Lactobacillus rogosae, Lactobacillus rossiae, Lactobacillus ruminis, Lactobacillus saerimneri, Lactobacillus sakei, Lactobacillus sakei* subsp. *carnosus, Lactobacillus sakei* subsp. *sakei, Lactobacillus salivarius, Lactobacillus salivarius* subsp. *salicinius, Lactobacillus salivarius* subsp. *salivarius, Lactobacillus sanfranciscensis, Lactobacillus saniviri, Lactobacillus satsumensis, Lactobacillus secaliphilus, Lactobacillus selangorensis, Lactobacillus senioris, Lactobacillus senmaizukei, Lactobacillus sharpeae, Lactobacillus shenzhenensis, Lactobacillus sicerae, Lactobacillus silagei, Lactobacillus silagincola, Lactobacillus siliginis, Lactobacillus similis, Lactobacillus sobrius, Lactobacillus songhuajiangensis, Lactobacillus spicheri, Lactobacillus sucicola, Lactobacillus suebicus, Lactobacillus sunkii, Lactobacillus suntoryeus, Lactobacillus taiwanensis, Lactobacillus thailandensis, Lactobacillus thermophilus, Lactobacillus thermotolerans, Lactobacillus timberlakei, Lactobacillus trichodes, Lactobacillus tucceti,*

*Lactobacillus uli, Lactobacillus ultunensis, Lactobacillus uvarum, Lactobacillus vaccinostercus, Lactobacillus vaginalis, Lactobacillus versmoldensis, Lactobacillus vespulae, Lactobacillus vini, Lactobacillus viridescens, Lactobacillus vitulinus, Lactobacillus vermiforme, Lactobacillus wasatchensis, Lactobacillus xiangfangensis, Lactobacillus xylosus, Lactobacillus yamanashiensis, Lactobacillus yamanashiensis* subsp. *mali, Lactobacillus yamanashiensis* subsp. *yamanashiensis, Lactobacillus yonginensis, Lactobacillus zeae, Lactobacillus zymae.*

In some embodiments, *Lactobacillus salivarius* (Ls) is administered to the patient.

In some embodiments, *Lactobacillus brevis* (Lb) is administered to the patient.

In some embodiments, at least 2, 3, 4 or 5 *Lactobacillus* strains are administered to the patient.

In some embodiments, *Lactobacillus paracasei, Lactobacillus salivarius* and *Lactobacillus brevis* (Lpsb or WL) are administered to the patient.

In some embodiments, *Lactobacillus salivarius* and *Lactobacillus brevis* are administered to the patient.

In some embodiments, the *Lactobacillus* strain is a probiotic strain. As used herein the term "probiotic" is meant to designate live microorganisms which, they are integrated in a sufficient amount, exert a positive effect on health, comfort and wellness beyond traditional nutritional effects. Probiotic microorganisms have been defined as "Live microorganisms which when administered in adequate amounts confer a health benefit on the host" (FAO/WHO 2001). As used herein the expression "probiotic *Lactobacillus* strain" denotes a *Lactobacillus* strain that has a beneficial effect on the health and well-being of the host.

In some embodiments, the probiotic *Lactobacillus* strain of the present invention is a viable probiotic *Lactobacillus* strain. The expression "viable probiotic *Lactobacillus* strain" means a microorganism which is metabolically active and that is able to colonize the respiratory tract of the subject.

Typically, the probiotic *Lactobacillus* strain of the present invention is produced with any appropriate culture medium well known in the art. Various fermentation media are suitable according to the invention, such as (but not limited to) e.g. firstly an industrial medium, in which the strain(s) is/are grown, and that is used as is or after concentration (e.g. drying) or after addition to another food base or product. Alternatively, bacterial cells, or bacterial cells with medium (e.g. the fermentation broth), or fractions of such cell comprising medium (i.e. medium with said bacterial strain/s) may be used. The cells or the cell comprising medium comprise live or viable bacterial cells and/or dead or non-viable bacterial cells of the strain(s). The medium may thus be treated by, but not limited to, heating or sonication. Also lyophilized, or frozen, bacteria and/or cell-free media (which may be concentrated) are encompassed in the methods for preparing the probiotic *Lactobacillus* strain of the present invention.

As used herein, the term "effective amount" refers to a quantity sufficient of the *Lactobacillus* strain to achieve the beneficial effect. In the context of the present invention, the amount of the *Lactobacillus* strain administered to the subject will depend on the characteristics of the individual, such as general health, age, sex, body weight . . . . The skilled artisan will be able to determine appropriate dosages depending on these and other factors. For example, the *Lactobacillus* strain shall be able to generate a colony is sufficient to generate a beneficial effect on the subject.

The composition comprising the effective amount of *Lactobacillus* may conveniently be administered by any method that allows administration to the respiratory tract (e.g. lungs). For example, nasal drops can be instilled in the nasal cavity by tilting the head back sufficiently and apply the drops into the nares. The drops may also be inhaled through the nose. Alternatively, a liquid preparation may be placed into an appropriate device so that it may be aerosolized for inhalation through the nasal or buccal cavity. For administration by inhalation the compositions may be delivered in the form of an aerosol spray presentation from pressurized packs or a nebulizer, with the use of a suitable propellant. Administered spray and drops can be a single dose or multiple doses. These procedures may involve mixing, granulating and compressing or dissolving the ingredients as appropriate to the desired preparation. It will be appreciated that the form and character of the pharmaceutically acceptable diluent is dictated by the amount of *Lactobacillus* active ingredient with which it is to be combined, the route of administration and other well-known variables. The carrier(s) must be "acceptable" in the sense of being compatible with the other ingredients of the formulation and not deleterious to the recipient thereof. "Carriers" or "vehicles" mean materials suitable for administration and include any such material known in the art such as, for example, any liquid, gel, solvent, liquid diluent, solubilizer, or the like, which is non-toxic and which does not interact with any components of the composition in a deleterious manner. Examples of nutritionally acceptable carriers include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethylcellulose, polyvinylpyrrolidone, and the like. Spray compositions for topical delivery to the lung by inhalation may for example be formulated as aqueous solutions or suspensions or as aerosols delivered from pressurized packs, such as a metered dose inhaler, with the use of a suitable liquefied propellant. Aerosol compositions suitable for inhalation can be either a suspension or a solution and generally contain the compositions of the present invention and a suitable propellant such as a fluorocarbon or hydrogen-containing chlorofluorocarbon or mixtures thereof, particularly hydrofluoroalkanes, e.g. dichlorodifluoromethane, trichlorofluoromethane, dichlorotetra-fluoroethane, especially 1, 1, 1,2-tetrafluoroethane, 1, 1, 1,2,3,3,3-heptafluoro-n-propane or a mixture thereof. Carbon dioxide or other suitable gas may also be used as propellant. The aerosol composition may be excipient free or may optionally contain additional formulation excipients well known in the art such as surfactants, e.g., oleic acid or lecithin and cosolvents, e.g. ethanol. Pressurized formulations will generally be retained in a canister (e.g. an aluminum canister) closed with a valve (e.g. a metering valve) and fitted into an actuator provided with a mouthpiece.

The invention will be further illustrated by the following figures and examples. However, these examples and figures should not be interpreted in any way as limiting the scope of the present invention.

FIGURES

FIG. 1: Pulmonary PA burden measured on total lung homogenates. Control PAO1, n=5 mice; SL (2 *L. fermentum* strains and 1 *L. rhamnosus* strains)+PAO1, n=5 mice; WL (1 *L. paracasei*, 1 *L. salivarius* and 1 *L. brevis* strains)+PAO1, n=4 mice.

FIG. 2: A) and B) Total white blood cell count in BALs at 6 h and 24 h post infection with PA. C) and D) Neutrophils ratio in BALs at 6 h and 24 h post infection with PA. Statistical significance: *, p<0.05. BAL: Bronchoalveolar lavage; PA: *P. aeruginosa*; WBC: White blood cells. Control PAO1, n=5 mice; SL (2 *L. fermentum* strains and 1 *L. rhamnosus* strains)+PAO1, n=5 mice; WL (1 *L. paracasei*, 1 *L. salivarius* and 1 *L. brevis* strains)+PAO1, n=4 mice.

Figure 3:
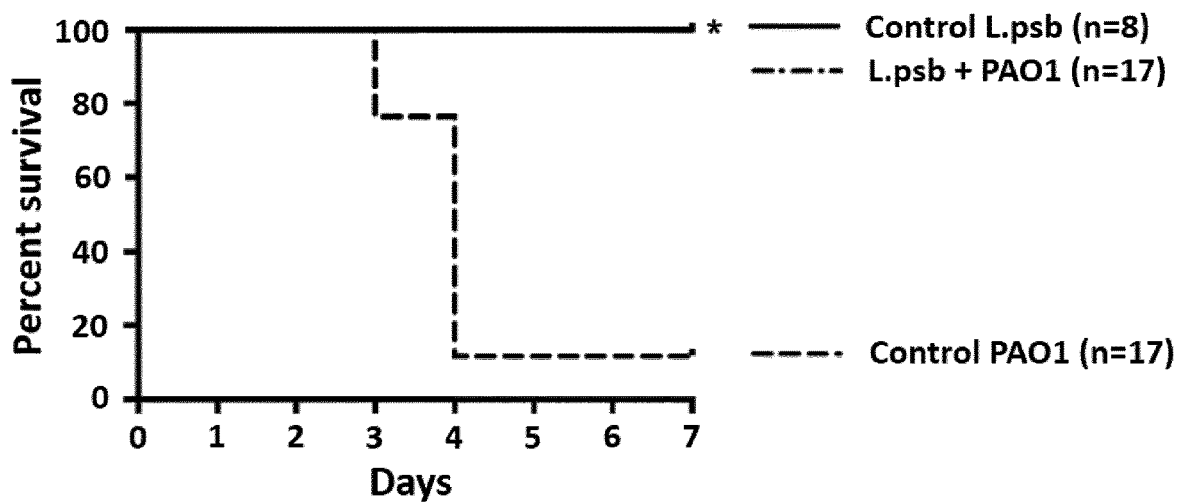

FIG. 3: Survival rate of mice. Priming of the respiratory tract with L.psb (1×10^6 CFU/mouse) resulted in survival in response to PA infection (2×10^6 CFU/mouse). Statistical significance: *, p<0.001 for the L.psb+PAO1 groups compared to the Control PAO1 group.

Figure 4:
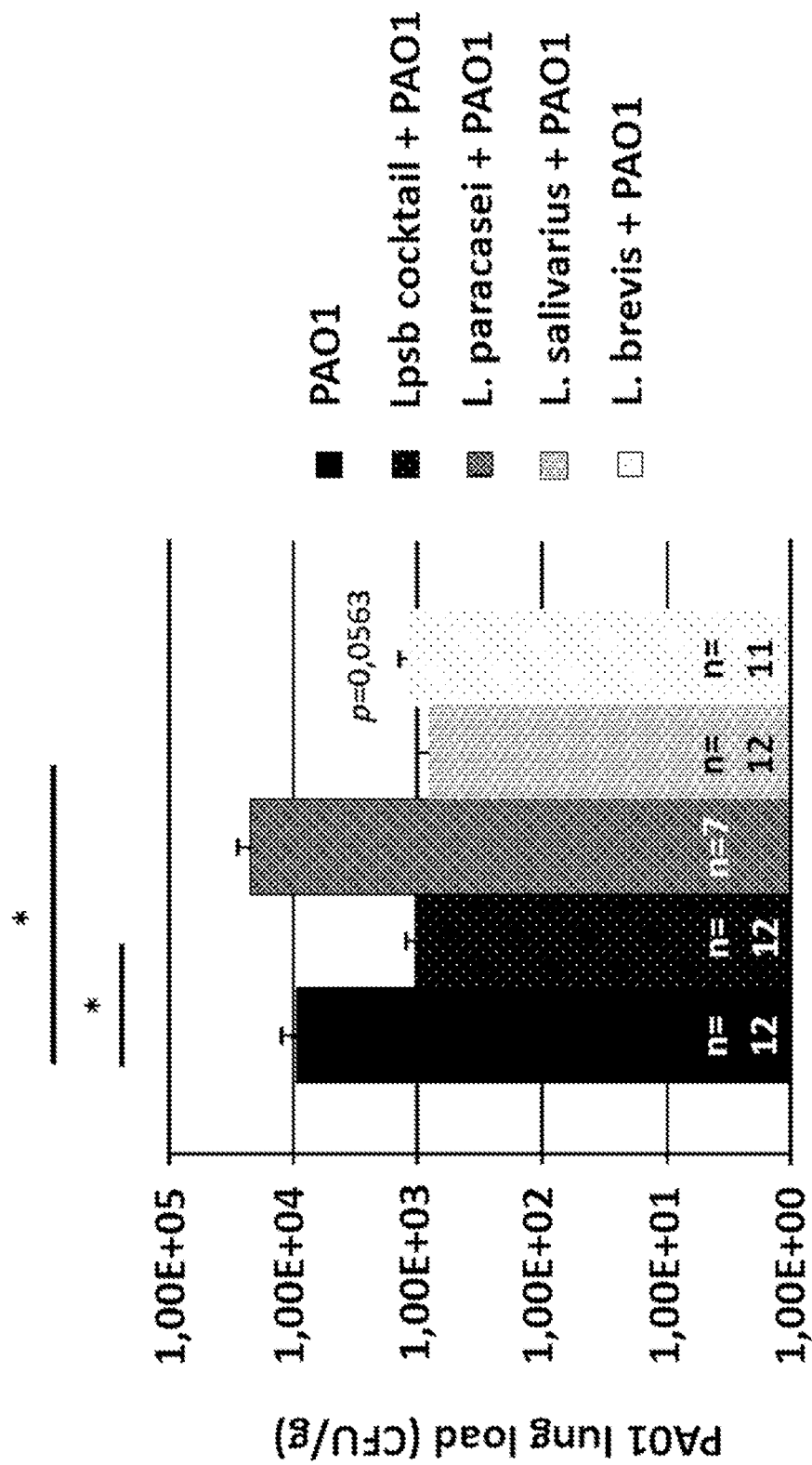

FIG. 4: PAO1 lung load in mice pre-treated with live *Lactobacillus* 24 h post-infection. Control PAO1, n=12 mice; Lpsb (*L. paracasei*, *L. salivarius* and *L. brevis*) cocktail+PAO1, n=12 mice; *L. paracasei*+PAO1, n=7 mice; *L. salivarius*+PAO1, n=12 mice; *L. brevis*+PAO1, n=11 mice.

EXAMPLE 1

Methods

Ethics

This study is approved by our local ethics committee and the ethics committee for animal experiments (DAP 2017040717237994).

Bacterial Strains

*Pseudomonas aeruginosa* Strain:

*P. aeruginosa* PAO1 was chosen as reference strain for all the experiments [1]. It was frozen at −80° C. before subculture on Mueller Hilton agar plate before the experiments.

*Lactobacillus* Strains:

One hundred and thirty-seven *Lactobacillus* isolates were previously isolated from CF patient's respiratory samples (Fangous et al, Research in Microbiology). Fifty *Lactobacillus* isolates were selected from PA colonised (n=30) or not colonised patients (n=20), by respecting the species prevalence observed within each group of patients. These isolates were screened in vitro for their ability to decrease the synthesis of 2 PA virulence factors, the pyocyanin and the elastase.

All isolates were frozen at −80° C. before subculture on 5% sheep-blood agar (bioMérieux, Marcy l'Etoile, France) in 5% $CO_2$ at 37° C. for 2 days before the experiments.

Inhibition Tests of *Lactobacillus* Strains on PAO1 Virulence Factors

Elastase

For the elastase assay, PAO1 and *Lactobacillus* isolates were cultivated overnight separately at 37° C. in Brain Heart Infusion broth (BHI). The inhibition of the elastolytic activity of *Pseudomonas aeruginosa* PAO1 by Lactobacilus isolates was investigated by colorimetric assay, using Elastin Congo Red (Sigma), as adapted by Alexandre and collaborators [2]. Succinctly, overnight culture of PAO1 in BHI broth was washed twice with isotonic saline solution and adjusted to $5×10^7$ CFU/ml in broth media. Overnight culture of *Lactobacillus* in BHI broth was neutralised with NaOH 0.1M and adjusted to $5×10^7$ CFU/ml in broth media. A vol/vol co-culture was made and incubated 20 hours under aerobic conditions at 37° C. After centrifugation (20' at 3500 g), 50 μL of the supernatant was mixed with 1 ml of Elastin Congo Red solution (20 mg/ml in a 10 mM sodium phosphate buffer) and incubated for 20 hours more under agitation. Finally, the soluble fraction released in the supernatant by elastase was measured at 495 nm after centrifugation (20' at 3500 g) with a spectrophotometer.

The results were normalized to the $OD_{595}$ of the co-culture and expressed as a ratio of the absorbance observed in presence of the *Lactobacillus* isolate to the absorbance observed with a monoculture of PAO1.

The experiments were conducted twice to three times for each isolate of *Lactobacillus*.

Pyocyanin

For pyocyanin production, *P. aeruginosa* PAO1 was grown overnight in Bacto-Peptone (BP) broth (20 mg/L BP, $MgCl_2$ 1.4 g/L, $K_2SO_4$ 10 g/L). *Lactobacillus* was grown overnight on MRS broth. A vol/vol co-culture was made as previously described for the elastase experiments, and incubate under aerobic conditions at 37° C. The inhibition of the pyocyanin synthesis was investigate by colorimetric assay after extraction in an acid solution as previously described [3].

The results were normalized to the $OD_{595}$ of the co-culture and expressed as a ratio of the absorbance observed in presence of the *Lactobacillus* isolate to the absorbance observed with a monoculture of PAO1.

The experiments were conducted twice to three times for each isolate of *Lactobacillus*.

Murine Model of Pneumonia:

Preparation of the Bacterial Strains

*Lactobacillus* were grown overnight on MRS broth under aerobic conditions at 37° C. The 3 strains of *Lactobacillus* with the better inhibitive abilities against *P. aeruginosa* PAO1 were equally mixed in a cocktail named "Strong Lactobacilli; SL".

The 3 strains with the weakest abilities were mixed and named "Weak Lactobacilli; WL".

*P. aeruginosa* PAO1 was grown overnight on Luria Bertani (LB) broth under aerobic conditions at 37° C.

Each culture was washed twice with isotonic saline solution and adjust to $10^8$ CFU/ml for the *P. aeruginosa* PAO1 suspension, or to $10^6$ CFU/ml for the SL and WL suspensions, based to the $OD_{595\ nm}$ and controlled by serial dilution and plating on Mueller Hinton agar plates in triplicates.

Animals

C57BL/6 mice, aged 6-8 weeks old, were purchased from Janvier Labs (Le Genest Saint Isle, France) and maintained at the University of Brest, France. Mice received water and food ad libitum, and were monitored every eight hours until being sacrificed.

Seventy-one mice were divided in 5 groups: Control, n=10; Control SL, n=16; Control PAO1, n=16; SL+PAO1, n=16; WL+PAO1, n=13.

Infection Model of Acute Pneumonia

Bacteria were administered by intranasal instillation of 20 μL of the bacterial suspension (10 μL per nostril), under a short intraperitoneal anaesthesia with ketamine/xylazine (100/10 mg/kg) allowing maintenance of spontaneous breathing.

*Lactobacillus* suspension (SL or WL) was administrated 18 hours prior the infection with *P. aeruginosa* PAO1.

Control groups received 20 μL of isotonic saline suspension instead of *Lactobacillus* suspension and/or *P. aeruginosa* suspension.

Sampling Procedure

Six or 24 hours post infection with PAO1, mice were anesthetized with intraperitoneal injection of ketamine/xylazine (100/10 mg/kg) and euthanasied by intracardiac exsanguination.

Blood, bronchoalveolar lavage (BAL), lung and spleen tissues were harvested from animals under aseptic conditions.

BAL was performed after euthanasia by cannulation of the trachea and injection and aspiration of 500 µl of isotonic saline solution three times.

Bacterial Loads

The lungs were removed and homogenized with 4 ml of isotonic saline solution with Ultra-Turrax. Bacterial loads of PAO1 and *Lactobacillus* cocktails were determined by plating serial dilutions of total lung homogenate on Cetrimide and MRS agar plate. Each dilution was plated in duplicate. Plates were incubated 24 to 48 h at 37° C. under aerobic conditions. Colonies were confirmed using MALDI-TOF mass spectrometry (Microflex LT, Bruker Daltonics, Bremen, Germany). Identifications were obtained when scores were strictly superior to 2.

White Blood Cells (WBC) Count

The total white blood cells count was enumerated by manual counting method with a hemocytometer by light microscopy.

Macrophages, neutrophils and lymphocytes were differentiated after centrifugation, cytospins preparation and May-Grünwald-Giemsa staining.

Cytokine Measurement

The concentrations of the cytokines were performed on BAL supernatant, after centrifugation at 4° C., and freezing at −80° C.

The cytokines studied were IL-1b, IL-12, IL-17-a, IL-22, IL-23, IFN-g and the 2 chimiokines CXCL-1 ad CXCL-2. Dosages were performed with single Elisa kits.

Statistics

Results are presented as mean and standard error of the mean. Comparisons between the groups were analysed by the Mann-Whitney test. Results were considered statistically significant for p<0.05. All statistical tests were performed using the R software.

Results

Screening In Vitro of *Lactobacillus* Strains

The 50 selected strains were distributed as figured on the Table 1. Eleven species were represented. Considering the anti-elastolytic activity, 25 (83%) strains from PA colonized patients and 15 (75%) strains from PA non colonized patients exhibited an anti-PA activity with respectively average of 60.6±0.15% and 64.7±0.15% of activity.

Considering the inhibition of the pyocyanin synthesis, 6 (20%) strains from PA colonized patients and 6 (30%) strains from PA non colonized patients exhibited an anti-PA activity with respectively average of 83.6±0.15% and 80.15±0.17% of activity.

To constitute 2 blends of *Lactobacillus* to administrated to our mice model of PA pneumonia, 3 strains with the better anti-PA activities and 3 strains with the weakest anti-PA activities were selected.

The "Strong Lactobacilli" (ST) blend was constituted with 2 *L. fermentum* strains and 1 *L. rhamnosus* strains. The three strains were from PA colonized patients.

The "Weak Lactobacilli" (WK) blend was constituted with 1 *L. paracasei*, 1 *L. salivarius* and 1 *L. brevis* strains. The last two strains were from PA colonized patients.

The anti-PA activity of these 6 strains are shown on the Table 2.

Administration of Lactobacilli Decreases the Lung PA Load

Significant decreases of 2 and 4 log of PAO1 were observed 24 h after PAO1 instillation in SL+PAO1 ($4.6.10^1$ CFU/g) and WL+PAO1 (<1 CFU/g) groups compared to PAO1 group ($6.8.10^4$ CFU/g) (FIG. 1). No increase in Lactobacilli load was observed whatever the group studied. However, Lactobacilli were still present in the lung 24 h after the instillation, with $1.16.10^4$ and $1.13.10^3$ CFU/g for the SL+PAO1 and WL+PAO1 groups respectively.

BAL Cytological Analysis

An increase of the WBC count and PNN were observed following the administration of the SL cocktail in the Control SL group, but significantly less important than in the Control PAO1 group (FIG. 2). A significant decrease of PNN in BAL was observed 6 h and 24 h post-infection in the two groups receiving prophylactic administration of *Lactobacillus* (SL+PAO1 and WL+PAO1 groups) compared to PAO1 group (FIG. 2).

BAL Cytokine Analysis

Following the decrease of the recruitment of PNN due to prophylactic administration of Lactobacilli cocktail, the immunological response was studied through cytokines and chemokines dosages 6 h (T6) and 24 h (T24) post PAO1 administration.

No production of CXCL1 and CXCL2 was observed in the Control and Control SL at T6 and T26 whereas an important increase was observed at Thin the Control PAO1 group. The chemokines CXCL1 and CXCL2 BAL's levels were decreased in SL+PAO1 (DNS) and WL+PAO1 groups (DS) at 6 h post-infection compared to the Control PAO1 group.

No difference of production of IL-1B was observed between the Control and Control SL groups at T6 and T24. However, an increase was observed at T6 in the Control PAO1 group (mean=115 pg/ml). The IL-1B BAL's level were decreased in SL+PAO1 (mean=67.5 pg/ml) and WL+PAO1 groups (mean=33.6 pg/ml; p=0.01) at 6 h post-infection compared to the Control PAO1 group. A significant decrease was also observed at T24 in the SL+PAO1 (mean=9.0 pg/ml; p=0.01) compared to Control PAO1 (mean=22.2 pg/ml).

No difference of production of IL-12 was observed between the Control, Control SL and Control PAO1 groups at T6. However, a slight increase was observed at T24 in the Control SL compared to the Control group, and a significant increase was observed in the PAO1 group (mean=105.5 pg/ml). No clear difference was observed in the SL+PAO1 and WL+PAO1 groups compared to Control PAO1 at T6 and T24.

No production of IFN-G was observed in the Control, Control SL and Control PAO1 at T6. However, an increase was observed in the Control PAO1 group at T24 (mean=77.7 pg/ml) compared to the 2 others. Following the administration of Lactobacilli cocktail, a decrease of IFN-G was observed at T24 in the SL+PAO1 (mean<15 pg/ml) and WL+PAO1 (mean<15 pg/ml) groups.

Finally, the immunomodulation mediated via the TH17 axis was explored through IL-17A and IL-23A dosages. No production of IL-17A was observed in the Control, Control SL and Control PAO1 at T6. However, an increase was observed in the Control PAO1 group at T24 (mean=96.4 pg/ml) compared to the 2 others. Following the administration of Lactobacilli cocktail, a decrease of IL-17A was observed at T24 in the SL+PAO1 (mean<5 pg/ml) and WL+PAO1 (mean=3.95 pg/ml) groups. A slight production of IL-23 was observed whatever the group at T6 and T24, with no significant difference following the prophylactic administration of Lactobacilli cocktails.

EXAMPLE 2

Methods

Ethics

This study has been approved by the ethics committee for animal experiments (DAP2017040717237994 and DAP2017110311134961).

Preparation of the Bacterial Strains

Lactobacilli were grown overnight on MRS broth under aerobic conditions at 37° C. Three strains without inhibitory activity were mixed as a control in a blend named "L.psb". PAO1 was grown overnight in Luria-Bertani broth (Sigma) under aerobic conditions at 37° C. Each culture was washed twice with isotonic saline solution (SS) and adjusted to 108 CFU.ml-1 for the PAO1 suspension, or to 107 CFU.ml-1 for the L.psb suspensions, based on the OD595 nm and controlled by serial dilution and plating on MH in triplicates.

Animals

C57BL/6 mice, aged 6-8 weeks old, were purchased from Janvier Labs (Le Genest Saint Isle, France) and maintained at the University of Brest, France. Mice received water and food ad libitum, and were monitored every eight hours until being sacrificed.

9 groups of C57BL/6 mice: Control PAO1, Control Lpsb (*L. paracasei, L. salivarius* and *L. brevis*), Control Lp (*L. paracasei*), Control Ls (*L. salivarius*), Control Lb (*L. brevis*), Lpsb+PAO1, Ls+PAO1 and Lb+PAO1.

Infection Model of Acute Pneumonia

Bacteria were administrated by intranasal instillation of 20 μL of the bacterial suspension (10 μL per nostril), under a short intraperitoneal anaesthesia with ketamine/xylazine (100/10 mg/kg) allowing maintenance of spontaneous breathing.

*Lactobacillus* suspension was administrated 18 hours prior the infection with *P. aeruginosa* PAO1.

Control groups PAO1 received isotonic saline suspension instead of *Lactobacillus* suspension. Control L.psb groups received isotonic saline suspension instead of PAO1.

Survival

Mice were monitored during 7 days after infection with PAO1. Fur aspect, activity, behaviour, posture, eye lids, respiration, chest sounds, and body weight were followed frequently during the whole experiment, and scored from 1 to 4 according to the M-CASS scoring system [17]. When mice reached a score of 11 during day, buprenorphine was administered subcutaneously (0.05 mg/kg/12 h) for analgesia. Mice were sacrificed when they reached a score of 4 in the 8 parameters during the day or in one parameter at night to prevent overnight death.

Sampling Procedure

Six (T6) or 24 hours (T24) post infection with PAO1, mice were anesthetized with intraperitoneal injection of ketamine/xylazine (100/10 mg/kg) and sacrificed by intracardiac exsanguination. Blood, BAL, lung and spleen tissues were harvested from animals under aseptic conditions. BAL was performed after euthanasia by cannulation of the trachea and injection and aspiration of 500 μl of SS three times.

Bacterial Cell Count in Lung Homogenates

Mice were sacrificed at T24 and lungs removed and homogenized with SS with Ultra-Turrax. Bacterial loads of PAO1 and *Lactobacillus* blends were determined by plating serial dilutions of total lung homogenate on Cetrimide (bioMérieux) and MRS agar plates. Each dilution was plated in duplicate. Plates were incubated 24 to 48 h at 37° C. under aerobic conditions. Colonies identification was confirmed using MALDITOF mass spectrometry (Microflex LT, Bruker Daltonics, Bremen, Germany).

White Blood Cells Count

The total white blood cells (WBC) count on BAL was enumerated by manual counting method with a hemocytometer (Kova slide) by light microscopy. Alveolar macrophages (AM), polymorphonuclear (PMN) and lymphocytes were differentiated after centrifugation, cytospins preparation and May-Grünwald-Giemsa staining.

Cytokine Measurement on BAL

The cytokines studied were IL-1β, IL-6, IL-1β, TNF-α, and the 2 chemokines CXCL-1 and CXCL-2. IL-1β, IL-6 and IL-10 (eBiosciences), TNF-α and the chemokines CXCL1 and CXCL2 (R&D System, Abingdon, UK) were determined in the BAL by enzyme-linked immunosorbent assay (ELISA), using commercial kits according to the manufacturer's recommendations. The lower levels of detection were 7 pg/ml for CXCL1 and CXCL2, 4 pg/ml for IL-1β and IL-6, 8 pg/ml for IL-10 and TNF-α.

Results

In Vitro Screening of Lactobacilli Isolated from CF Respiratory Samples

Forty strains (80%) exhibited anti-elastolytic activity (mean activity=−37.4%±0.15), and 12 (24%) exhibited anti-pyocyanin activity (mean activity=−18.13%±0.15). To constitute 2 blends of Lactobacilli to administrate to the mice model of PA pneumonia, 3 strains with the highest anti-PA activities (L.rff) and 3 strains with no anti-PA activities (L.psb) were selected (Table 2).

"L.rff" was constituted with 2 *L. fermentum* strains and 1 *L. rhamnosus* strain. The three strains were isolated in PA colonised patients.

"L.psb" was constituted with 1 *L. paracasei*, 1 *L. salivarius* and 1 *L. brevis* strains. The last two strains were isolated in PA colonised patients.

Nasal Priming with Lactobacilli Enhances the Survival Rate

C57BL/6 mice were inoculated intranasally with each blend of Lactobacilli 18 hours prior to PAO1 administration. All Control PAO1 mice died but two (12% survival). Mice receiving L.psb were fully protected (100% survival) ($p<0.001$). None of the Control L.psb mice died nor exhibited any clinical signs of distress (FIG. 3).

Administration of Lactobacilli Decreases the Lung PA Load

Significant decrease of PAO1 lung load observed 24 h postinfection in presence of Lpsb cocktail ($9.49\times10^2$ CFU/g, $p=0.010$) and Ls strain ($7.81\times10^2$ CFU/g $p=0.011$) whereas a moderate impact of Lb strain ($1.16\times10^3$ CFU/g $p=0.056$) is observed compared to the control PAO1 group ($9.34\times10^3$ CFU/g) (FIG. 4).

White Blood Cells Count and Cytokines Analysis in BAL

To elucidate the mechanism of the PA lung load reduction, we investigated the WBC recruitment and cytokine synthesis in the BAL (FIG. 2). Control L.rff group significantly recruited more WBC at T6 and T24 compared to sham mice ($p<0.01$). This infiltrate was mostly composed of PMN whereas the BAL of sham mice only included AM. As expected, mice from the Control PAO1 group exhibited a strong increased number of WBC which was mainly composed of neutrophils. This recruitment is significantly more important (3 and 9 times more respectively at T6 and T24) than in the control L.rff mice. A significant decreased of PMN in BAL was observed at T6 and T24 in the L.rff+PAO1 and L.psb+PA01 groups compared to PAO1 group. We investigated the immunological response due to prophylactic administration of Lactobacilli blend through cytokines and chemokines dosages in the BAL. Administration of Lactobacilli alone did not induce the secretion of CXCL1, CXCL2, IL-1β, IL-6 and TNF-α compared to sham mice. Infection of PAO1 induced a cytokine burst particularly at 6 h. Prophylactic administration of Lactobacilli leads to lower secretions of chemokines CXCL1 and CXCL2 (at T6) and proinflammatory cytokines IL-1β, IL-6 and TNF-α (both at T6 and T24) in both L.rff+PAO1 and L.psb+PA01 groups compared to the Control PAO1 group (Data not shown). The IL-10 production was significantly increased in the L.psb group compared to the Control PAO1 groups (Data not shown) but no difference was observed with the sham group.

DISCUSSION

Intranasal administration of Lactobacilli improves lung *P. aeruginosa* clearance at 24 hours post infection, associated with the decrease of chemokines and proinflammatory cytokines, and a lower neutrophils recruitment.

Used as a prophylactic treatment, Lactobacilli reduce the inflammatory response triggered by PA, which is deleterious on the PA control group. No difference in the PA lung load, white blood cells count or cytokines production was observed between the 2 blends of Lactobacilli administered. This might suggest that there is no correlation between the anti-PA activities screened in vitro on *Lactobacillus* strains and their abilities to fight against the infection in vivo. The two virulence factors studied for the screening, the elastase and pyocyanin, were chosen because their pathogenicity was confirmed in vivo on murine model of pneumonia (Le Berre et Lau, 2004). Thus, the elastolytic activity was positively correlated to acute lung injury, and PA pyocyanin deficient isogenic mutants induce less tissue damages than the wild strains. As no difference was observed in our study whatever the anti-PA activities of the *Lactobacillus* strains used, both virulence factors which are quorum sensing dependent probably not interfere directly with the innate immune response in our murine model of PA pneumonia, and nor is the quorum sensing system.

Considering the different mechanisms of action of the probiotics, direct antimicrobial activity, reinforcement of the epithelium barrier function and immunomodulation (Alexandre, 2014), other hypothesis than the inhibition of the PA virulence factors must be formulated to understand how Lactobacilli may act against PA infection. Several publications studying the effect of *Lactobacillus* administration by oral gavage suggest that the probiotic protective abilities of *Lactobacillus* are based on the immunomodulation mediated by the gut-lung axis. However, in our study, Lactobacilli were administrated intranasally to liberate from this axis and observed their action on the respiratory tract when directly administered in situ. Nevertheless, similarities probably exist, as the microbiota modification occurring in the gut and leading to the immunomodulation which certainly occurs in the lung too. Lactobacilli could sufficiently stimulate the respiratory mucosal immune system to protect from bacterial infection.

In our study, the PA clearance lead by the Lactobacilli may be based on the modulation of the bactericidal activity and phagocytosis activity of the alveolar macrophage and neutrophils, which recruitment is decreased and associated with a lightest production of chemokines when Lactobacilli were administrated compared to the PAO1 group.

CONCLUSION

The administration of Lactobacilli cocktail 18 h prior the PA lung infection decreases significantly the lung bacterial load at 24 h post-infection. Although the mechanisms need to be deeply explored, an immunomodulation effect may be involved, notably through the recruitment of PNN.

Tables:

TABLE 1

*Lactobacillus* strains selected for the in vitro screening

| Patients status of PA colonization | Species | Number of strains |
|---|---|---|
| Colonized | L. rhamnosus | 9 |
|  | L. fermentum | 6 |
|  | L. paracasei | 5 |
|  | L. gasseri | 3 |
|  | L. salivarius | 1 |
|  | L. crispatus | 1 |
|  | L. johnsonii | 1 |
|  | L. brevis | 1 |
|  | L. parabuchneri | 1 |
|  | L. casei | 1 |
|  | L. plantarum | 1 |
| Non colonized | L. rhamnosus | 5 |
|  | L. fermentum | 4 |
|  | L. paracasei | 4 |
|  | L. salivarius | 2 |
|  | L. parabuchneri | 1 |
|  | L. plantarum | 1 |
|  | L. gasseri | 2 |
|  | L. johnsonii | 1 |

TABLE 2 anti-PA activities of the 6 *Lactobacillus* strains selected to be administrated to the mice (expressed as a ratio of the absorbance observed in presence of the *Lactobacillus* isolate to the absorbance observed with a monoculture of PAO1).

| Blend of *Lactobacillus* | Strains of *Lactobacillus* | Anti-elastolytic activity (%) | Anti-pyocyanin synthesis (%) |
|---|---|---|---|
| "Strong *Lactobacilli*" | L. rhamnosus 2C | 61 | 71 |
|  | L. fermentum 9C | 50 | 94 |
|  | L. fermentum 10C | 69 | 76 |
| "Weak *Lactobacilli*" | L. paracasei 9N | 114 | 116 |
|  | L. salivarius 20C | 187 | 150 |
|  | L. brevis 24C | 141 | 174 |

REFERENCES

Throughout this application, various references describe the state of the art to which this invention pertains. The disclosures of these references are hereby incorporated by reference into the present disclosure.

The invention claimed is:

1. A method of treating a *Pseudomonas aeruginosa* respiratory tract infection in a patient in need thereof comprising administering to the patient's respiratory tract a therapeutically effective amount of at least one *Lactobacillus* strain, wherein the administration is performed by instillation or inhalation.

2. The method of claim 1 wherein the patient suffers from a chronic pulmonary disease selected from the group consisting of chronic obstructive pulmonary disease (COPD), ventilated acquired pneumonia, chronic bronchitis, recurrent bronchitis, acute bronchitis, rhinosinusitis, mild pulmonary disease, hereditary emphysema, and cystic fibrosis.

3. The method of claim 1 wherein the *Lactobacillus* strain is selected from the group consisting of *Lactobacillus acetotolerans, Lactobacillus acidipiscis, Lactobacillus acidophilus, Lactobacillus agilis, Lactobacillus algidus, Lactobacil-* lus alimentarius, Lactobacillus amylolyticus, Lactobacillus amylophilus, Lactobacillus amylovorus, Lactobacillus animalis, Lactobacillus arizonensis, Lactobacillus aviarius, Lactobacillus bifermentans, Lactobacillus brevis, Lactobacillus buchneri, Lactobacillus casei, Lactobacillus coelohominis, Lactobacillus collinoides, Lactobacillus coryniformis subsp. coryniformis, Lactobacillus coryniformis subsp. torquens, Lactobacillus crispatus, Lactobacillus curvatus, Lactobacillus cypricasei, Lactobacillus delbrueckii subsp. bulgaricus, Lactobacillus delbrueckii subsp delbrueckii, Lactobacillus delbrueckii subsp. lactis, Lactobacillus durianus, Lactobacillus equi, Lactobacillus farciminis, Lactobacillus ferintoshensis, Lactobacillus fermentum, Lactobacillus formicalis, Lactobacillus fructivorans, Lactobacillus frumenti, Lactobacillus fuchuensis, Lactobacillus gallinarum, Lactobacillus gasseri, Lactobacillus graminis, Lactobacillus hamsteri, Lactobacillus helveticus, Lactobacillus helveticus subsp. jugurti, Lactobacillus heterohiochii, Lactobacillus hilgardii, Lactobacillus homohiochii, Lactobacillus intestinalis, Lactobacillus japonicus, Lactobacillus jensenii, Lactobacillus johnsonii, Lactobacillus kefiri, Lactobacillus kimchii, Lactobacillus kunkeei, Lactobacillus leichmannii, Lactobacillus letivazi, Lactobacillus lindneri, Lactobacillus malefermentans, Lactobacillus mali, Lactobacillus maltaromicus, Lactobacillus manihotivorans, Lactobacillus mindensis, Lactobacillus mucosae, Lactobacillus murinus, Lactobacillus nagelii, Lactobacillus oris, Lactobacillus panis, Lactobacillus pantheri, Lactobacillus parabuchneri, Lactobacillus paracasei subsp. paracasei, Lactobacillus paracasei subsp. pseudoplantarum, Lactobacillus paracasei subsp. tolerans, Lactobacillus parakefiri, Lactobacillus paralimentarius, Lactobacillus paraplantarum, Lactobacillus pentosus, Lactobacillus perolens, Lactobacillus plantarum, Lactobacillus pontis, Lactobacillus psittaci, Lactobacillus reuteri, Lactobacillus rhamnosus, Lactobacillus ruminis, Lactobacillus sakei, Lactobacillus salivarius, Lactobacillus salivarius subsp. salicinius, Lactobacillus salivarius subsp. salivarius, Lactobacillus sanfranciscensis, Lactobacillus sharpeae, Lactobacillus suebicus, Lactobacillus thermophilus, Lactobacillus thermotolerans, Lactobacillus vaccinostercus, Lactobacillus vaginalis, Lactobacillus versmoldensis, Lactobacillus vitulinus, Lactobacillus vermiforme, Lactobacillus zeae.

4. The method of claim 1 wherein at least 2, 3, 4 or 5 *Lactobacillus* strains are administered to the patient.

5. The method of claim 1 wherein *Lactobacillus salivarius* and *Lactobacillus brevis* are administered to the patient.

6. The method of claim 1 wherein the *Lactobacillus* strain is a probiotic strain.

7. The method of claim 1 wherein the probiotic *Lactobacillus* strain is a viable probiotic *Lactobacillus* strain.

\* \* \* \* \*